United States Patent
Hyson

(10) Patent No.: US 6,313,370 B1
(45) Date of Patent: Nov. 6, 2001

(54) MEDICATED WRAP

(76) Inventor: Morton Hyson, 2020 Goldring #402, Las Vegas, NV (US) 89106

( * ) Notice: Subject to any disclaimer, the term of this patent is extended or adjusted under 35 U.S.C. 154(b) by 0 days.

(21) Appl. No.: 09/561,170

(22) Filed: Apr. 27, 2000

Related U.S. Application Data

(60) Provisional application No. 60/131,857, filed on Apr. 29, 1999.

(51) Int. Cl.[7] .............................. A61F 5/00; A61F 13/00
(52) U.S. Cl. ................................ 602/48; 602/60; 602/61; 602/62; 602/64; 602/18; 602/53
(58) Field of Search .................................. 602/18, 26, 21, 602/60, 61, 64, 75, 41, 42, 43, 46, 57; 601/33; 606/201, 203, 204, 204.15; 2/455, 42, 24, 16

(56) References Cited

U.S. PATENT DOCUMENTS

| | | |
|---|---|---|
| 699,897 | 5/1902 | Ray . |
| 865,254 | 9/1907 | Kappmeier . |
| 924,596 | 6/1909 | Blashfield . |
| 1,150,526 | 8/1915 | Leitheiser . |
| 1,250,273 | 12/1917 | Brady . |
| 1,324,975 | 12/1919 | Morris . |
| 1,481,354 | 1/1924 | Dingfeld . |
| 1,607,717 | 11/1926 | Nagler et al. . |
| 1,642,661 | 9/1927 | Robinson . |
| 1,758,764 | 5/1930 | Roxburg . |
| 1,823,686 | 9/1931 | Hanke . |
| 2,101,628 | 12/1937 | Padelford . |
| 2,543,104 | 2/1951 | Golding . |
| 3,092,103 | 6/1963 | Mower . |
| 3,884,240 * | 5/1975 | Gilman ................................ 602/53 |
| 4,005,709 * | 2/1977 | Laerdal ................................ 602/53 |
| 4,117,842 | 10/1978 | Hutchins . |
| 4,307,717 | 12/1981 | Hymes et al. . |
| 4,473,370 | 9/1984 | Weiss . |
| 4,632,104 | 12/1986 | Conrow . |
| 4,675,009 | 6/1987 | Hymes et al. . |
| 4,677,974 | 7/1987 | Leonardi . |
| 4,790,031 | 12/1988 | Duerer . |
| 4,976,705 | 12/1990 | Aki et al. . |
| 5,312,350 * | 5/1994 | Jacobs ................................. 604/116 |
| 5,486,194 * | 1/1996 | Kawasaki et al. .................... 606/203 |
| 5,536,263 | 7/1996 | Rolf et al. . |
| 5,538,500 * | 7/1996 | Peterson ............................... 602/48 |
| 5,667,484 * | 9/1997 | Brossard .............................. 602/21 |
| 5,690,610 * | 11/1997 | Ito et al. .............................. 602/53 |
| 5,695,520 * | 12/1997 | Bruckner et al. .................... 606/204 |
| 5,848,981 * | 12/1998 | Herberanson ........................ 601/134 |
| 5,944,682 * | 8/1999 | Milana-Panopoulos ............... 602/62 |
| 6,048,326 * | 4/2000 | Davis et al. .......................... 602/26 |
| 6,077,242 * | 6/2000 | Falk et al. ............................ 602/62 |

* cited by examiner

*Primary Examiner*—Kim M. Lewis
(74) *Attorney, Agent, or Firm*—Pennie & Edmonds LLP

(57) ABSTRACT

A device for treating pain in an injured body member includes a wrap having an interior section which can loaded with medicament. The wrap also includes at least one inwardly extending nodule adapted to exert pressure on and compress a specific area of the injured member, having acupressure like effect in producing pain relief. The wrap has adjustable means for fastening the wrap around the body member, thereby enabling the wearer to exert a specific amount of pressure sufficient to dispense medicament from the interior pad and to adjust the pressure on the nodule to achieve the desired results. The combination of restricted movement imparted by the wrap along with the medicament and acupressure, affords the wearer more rapid pain relief than any of the treatments combined.

9 Claims, 3 Drawing Sheets

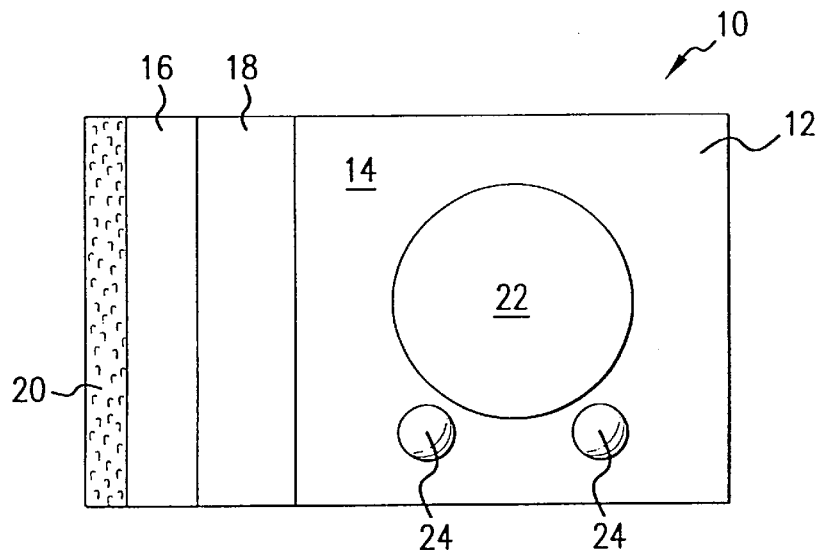
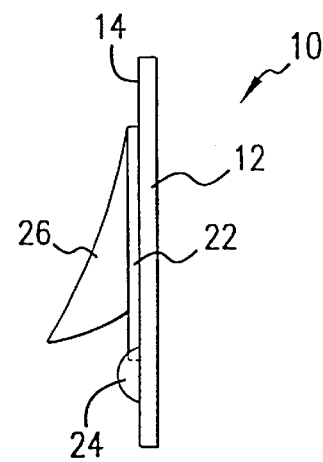
FIG.1
FIG.3
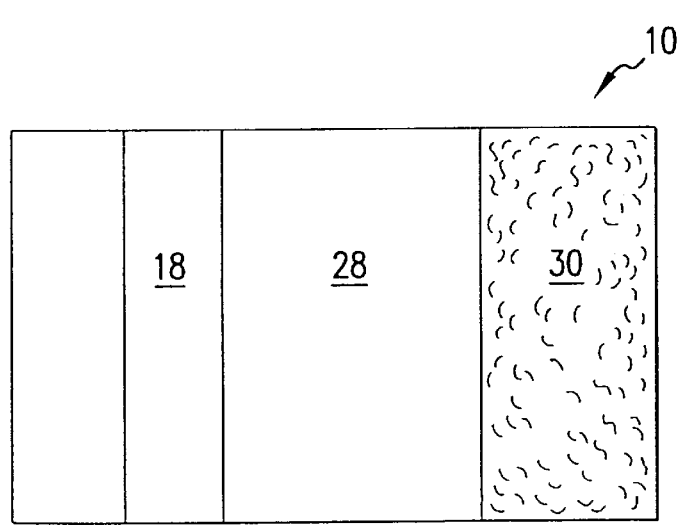
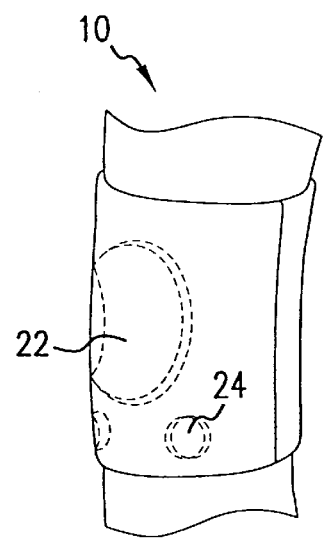
FIG.2
FIG.4

MEDICATED WRAP

RELATED APPLICATION DATA

The present application claims priority to provisional application Ser. No. 60/131,857, filed Apr. 29, 1999, by Applicant herein.

FIELD OF THE INVENTION

The present invention relates to a medical device for relieving pain by simultaneously restricting movement of a body member by applying pain-relieving medicament, and applying pressure to acupressure points.

BACKGROUND

Many people suffer from sprains, arthritis and other ailments at the joints such as the knees, elbows, wrists as well as neck pain. Often the treatment consists of wraps to stabilize and provide pressure to the joint, sports ointments and creams as well as prescribed and over-the-counter pain medications.

Many people suffering from such ailments are reluctant to take pain killing drugs over an extended period of time for fear of obtaining a dependency or simply based upon a general reluctance to take drugs. For these people, the remedies are limited to treatment through ice, heat, wraps and externally applied ointments such as sports creams and the like. The products such as wraps and ointments must be separately purchased. Further, the ointments and creams, if applied underneath a wrap, can stain and soil the wrap making it unsightly for the person to wear in public.

Still further, it is known that certain pressure joints near joints, if pressure is applied, can help to reduce and alleviate pain. The wraps and ointments heretofore used do not provide a means to impose an acupressure effect to help reduce pain.

The present invention is directed to overcome these drawbacks.

SUMMARY OF THE INVENTION

The invention provides a device for treating pain in an injured body portion which includes a flexible, elastic wrap which can be secured in place around the body portion. The wrap has an interior surface which includes an absorbent pad section designed to be loaded with medicament. The pad section can come preloaded with medicament, in which case the pad is covered by a removable impervious cover element. At least one, and preferably at least two substantially rigid nodules project inwardly from the wrap and are disposed to contact predetermined areas of the injured member. The nodules are located strategically to provide acupressure-like force against specific acupressure points thereby compressing the point and providing additional pain relief.

The wrap has adjustable fastening means, such as Velcro® hook and loop fasteners, so that the user can stretch the wrap around the injured part and adjust the pressure so as to dispense medicament to the affected area and to select the desired pressure at the acupressure points.

BRIEF DESCRIPTION OF THE DRAWINGS

FIG. 1 is a bottom view of a wrap according to one embodiment of the present invention adapted for joints as knees and elbows as well as the back;

FIG. 2 is a top view of the wrap of FIG. 1;

FIG. 3 is a side view of the wrap of FIG. 1;

FIG. 4 is a view of the wrap of FIG. 1 applied around a knee;

DESCRIPTION

Figure 5:
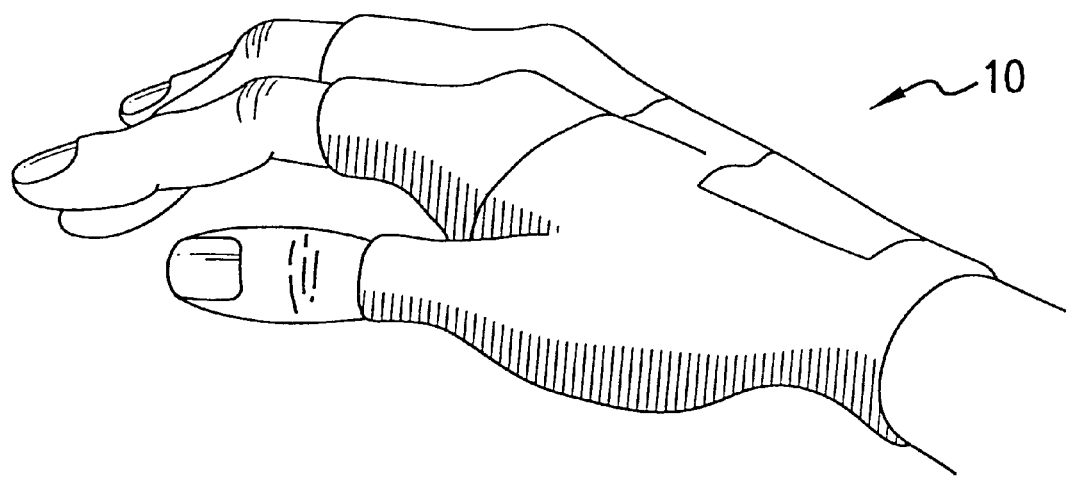
FIG. 5 is a wrap according to another embodiment of the present invention for treatment of the wrist.

Turning to the drawings, FIG. 1 shows a wrap 10 according to one embodiment of the present invention. The wrap 10 has an underside 12 adapted to be positioned against the skin when the wrap is used to treat a joint such as a knee or elbow or it can be of a size to wrap about the trunk of the body to treat the back. The wrap itself includes a main panel 14 connected to a side panel 16 by an elastic margin 18. At the end of the side panel 16 is one member 20 of a hook and pile fastener for securing the wrap 10 about the joint.

Disposed on the body 14 is a pad 22 adapted to receive and store topical medication for treatment of pain. The topical treatment may include analgesics such as lidocaine, Trolamine, Salicylate, aspirin creams or any suitable prescriptive or non-prescriptive applied analgesic or anesthetic cream. As shown in FIG. 3, if the pad 22 is loaded with the medicament by the manufacturer, a tear-away cover sheet 26 may be provided by which the user may tear away the protective cover to expose the pad 22 loaded with the medicament. The use of a tear-away cover is conventional technology.

The wrap 10 may also include one or more acupressure nodules 24 located to engage pressure points in the joint, muscle or ligament area to apply pressure thereto for the treatment of pain. As shown in FIG. 3, these nodules 24 may be spherical in shape and may be manufactured from a rigid product such as rubber, plastic or the like.

With reference to FIG. 2, at the top side 28 of the wrap 10 there is located the other member 30 for the hook and pile fastener for the wrap 10. Accordingly, and with reference to FIG. 4, the user would remove the protective strip or cover 26 to expose the pad 22 pre-loaded with medicament. The user would then place the pad 22 over, for example, the patella and position the wrap 10 about the knee joint securing it thereto using the members 20, 30 of the hook and pile fastener. The elastic margin 18 enables the user to exert pressure by constricting or releasing the pressure imposed by the wrap 10 on the knee joint. In this position, as suggested in FIG. 4, the nodules 24 are disposed to the side and below the patella to exert acupressure effect on the ligaments of the knee joint.

Figure 6:
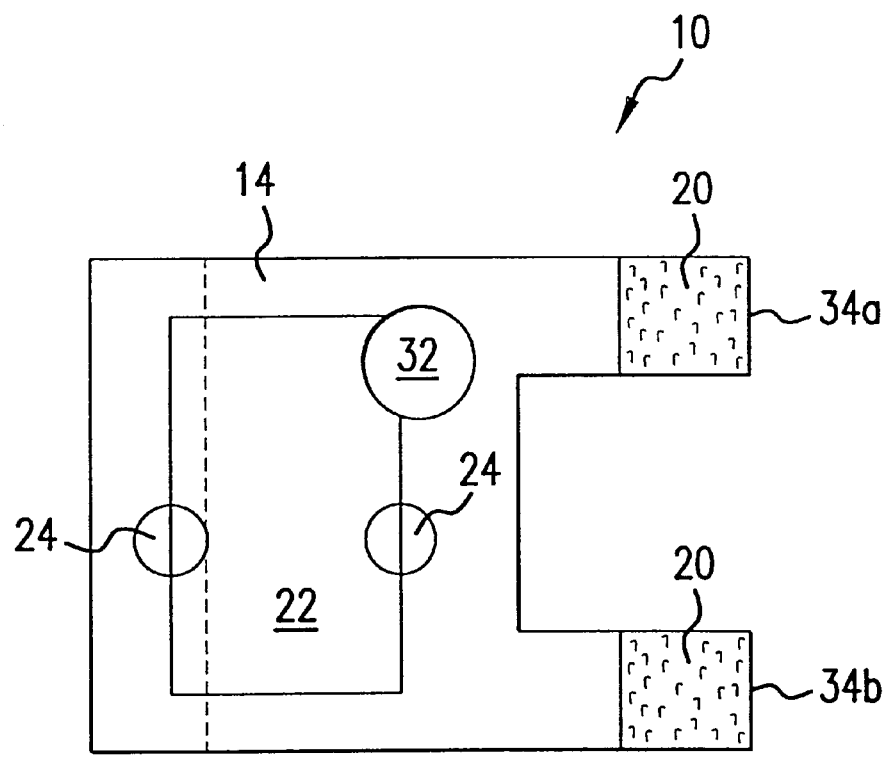
FIG. 6 is the view of the underside of the wrap of FIG. 5.

Turning to FIGS. 5 and 6, a further embodiment of the wrap 10 for use at the wrist is shown. The wrap 10 includes the main panel 14 including the pad 22 to receive the medicament. A hole 32 is provided to pass the thumb when the wrap 10 is disposed about the wrist. Acupressure nodules 24 are provided to exert pressure at desired locations on the wrist. Straps 34a,b include the one member 20 of a hook and pile fastener, the other member 30 (not shown in FIGS. 5 and 6) of the hook and pile fastener is disposed on the outside surface of the wrap 10.

Figure 7:
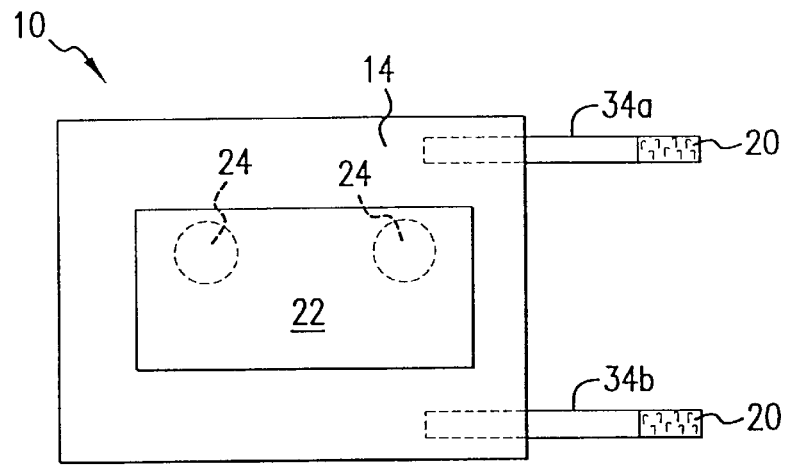
FIG. 7 is the view of the underside of a wrap according to yet another embodiment of the present invention directed for use around the neck to treat the cervical area.
Figure 8:
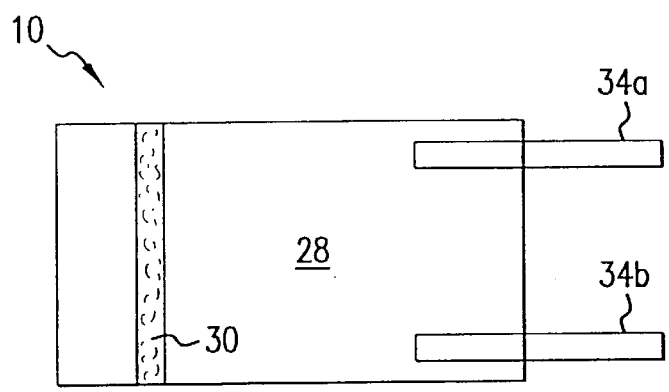
FIG. 8 is a view of the top of the wrap of FIG. 7.
Figure 9:
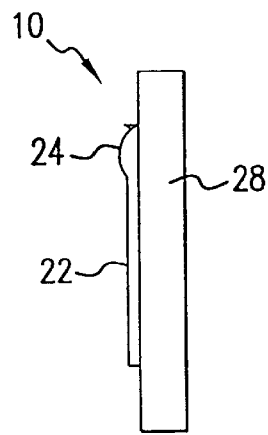
FIG. 9 is a side view of the wrap.

Turning to FIGS. 7–9, an embodiment of the wrap 10 for cervical use is disclosed. The wrap 10 includes the main panel 14 having the pad 22 to retain the medicament.

Acupressure nodules 24 are provided to exert pressure at desired locations at the neck. The top side 28 includes the other member 30 of the hook and pile fastener. Straps 34a,b include the member 20 for the hook and pile fastener. Accordingly the wrap 10 is wrapped about the neck placing the pad 22 at the desired location to apply the medicament.

At least one nodule is provided on the interior of each wrap, and can be molded, sewn, welded, or otherwise secured to the interior surface of the wrap. The nodules are located on specific portions of the wrap in predetermined areas designed to correspond with known acupressure points for that specific body portion. These acupressure points are well-known and readily identifiable from medical literature, and may be adjacent areas of pain rather than directly on the pain. The nodules should be generally rigid, so that pressure can be applied quite specifically to the desired region of the member in which pain is being suffered. The nodules should have a generally curved surface, so as to not be pointed or have other sharp edges or protrusions that could injure the patient. The specific size of the nodule is not critical, although the area contacting the body should be sufficiently large so as to not create additional pain (e.g. by puncturing or sharply compressing the skin), but should not be so large as to distribute the pressure over a wider area than is necessary. Generally speaking, the area being compressed should be approximately ¼–¾ inch in diameter, depending on the specific area of the body involved. Examples of suitable nodules would be spherical lugs having a diameter of ¼–¾ inch, preferably about ½ inch, though other shapes and dimensions may be usable depending upon the specific body part. For example, smaller nodules would be used for a wrist wrap, whereas larger nodules might be used for wraps for the knee or back. The nodules can be made from a generally rigid material such as hard rubber, but may have a small amount of resiliency (e.g. less than 10%) which could provide some patient comfort while not compromising the ability of the nodules to exert pressure.

The method of pain relief afforded by the invention is implemented by a user either loading the absorbent pad with medicament or removing the plastic impervious cover to expose pre-loaded medicament. Next, the user (or someone who assists the user) extends the wrap around the injured body portion, locating the nodules above the desired acupressure points. Then the wrap is tightened until the nodules exert pressure at the desired location which is sufficient to substantially compress the desired spot yet not cause additional pain. At this point, the adjustable fastening members are attached to retain the desired pressure. The tightened wrap restricts the mobility of the injured limb, thereby promoting healing. Furthermore, the tightened pressure is sufficient to exert force on the acupressure point and exude medicament from the pad into the area of treatment. These three desired affects combined enable the wearer to heal more quickly in a pain-free environment.

After wearing the wrap for a certain period of time, the user may become accustomed to the pressure of the acupressure nodules and desire to increase the pressure, thereby increasing the effectiveness of the nodules. The releasable fastener is then released, the wrap is tightened, and the adjustable fastening members are re-attached.

The pad may be any sort of absorbent material, such as sponge, cotton or synthetic fiber, or any other known material which can hold a fluid product. The wrap may be disposable, or may be reusable in which case the pad can be reloaded by the user with medicament prior to each use.

I claim:

1. A device to be disposed around a body portion of a person for treating pain in said body portion comprising a wrap having an interior surface for contacting the body portion, and adapted to be disposed around the body portion, said wrap being sufficiently elastic to enable the wrap to be stretched around the body portion to restrict the mobility of the body portion, at least one absorbent first region secured to an interior section of the wrap, each region adapted to be loaded with medicament, at least one nodule extending inwardly from the interior surface of the wrap and adapted to contact and exert pressure at a desired specific location on the body portion, and means for tightening and adjustably securing the wrap about the,body portion, whereby tightening of the wrap causes medicament to exert pressure on and dispense medicament to the area of pain, and to cause the nodule to exert pressure upon the body portion.

2. The device of claim 1 having at least two substantially rigid nodules extending inwardly from the interior surface of the wrap.

3. The device of claim 1 having at least two substantially rigid nodules extending inwardly from the interior surface of the wrap, and located on the wrap such that when the wrap is in place around the body portion, the nodules contact predetermined known acupressure points.

4. The device of claim 1 wherein each nodule is a substantially rigid member having a curved contact surface of from approximately ¼" to approximately ¾" in diameter.

5. The device of claim 1 wherein the medicament is lidocaine.

6. A method of relieving pain in a body portion comprising extending a flexible wrap around the injured body portion, said wrap having an absorbent interior region loaded with medicament and at least one substantially rigid nodule extending inwardly and adapted to contact pre-located acupressure points near the area of the pain, locating the nodule above the acupressure point, and tightening and adjustably securing the wrap such that mobility of the body portion is decreased, pressure is exerted by the nodule on the desired acupressure point, and medicament is dispensed to the are of pain.

7. The method of claim 6 wherein the device comprises at least two nodules, and all of the nodules are located above acupressure points.

8. The method of claim 6 wherein the medicament is lidocaine.

9. The method of claim 6 wherein the device has at least two substantially rigid nodules, each of which has a curved contact surface of approximately ¼" to approximately ¾" in diameter.

* * * * *